United States Patent [19]
Johnson, Jr.

[11] 3,940,689
[45] Feb. 24, 1976

[54] COMBINED EDDY CURRENT AND LEAKAGE FIELD DETECTOR FOR WELL BORE PIPING USING A UNIQUE MAGNETIZER CORE STRUCTURE

[75] Inventor: Wade M. Johnson, Jr., Los Alamos, N. Mex.

[73] Assignee: Schlumberger Technology Corporation, New York, N.Y.

[22] Filed: May 14, 1974

[21] Appl. No.: 469,935

[52] U.S. Cl. ............................................... 324/37
[51] Int. Cl.² ........................................ G01R 33/12
[58] Field of Search .......... 324/34 R, 34 TK, 37, 40

[56] References Cited
UNITED STATES PATENTS

| | | | |
|---|---|---|---|
| 2,573,799 | 11/1951 | MacLean | 324/37 |
| 3,271,664 | 9/1966 | Mountz et al. | 324/40 |
| 3,437,810 | 4/1969 | Wood et al. | 324/37 |
| 3,543,144 | 11/1970 | Walters et al. | 324/37 |
| 3,597,678 | 8/1971 | Fearon | 324/37 |

Primary Examiner—Robert J. Corcoran
Attorney, Agent, or Firm—Ernest R. Archambeau, Jr.; William R. Sherman; Stewart F. Moore

[57] ABSTRACT

In the representative embodiment of the present invention disclosed herein, new and improved pipe-inspection apparatus for examining oilfield piping includes, along with other flaw-inspection devices, a flux-leakage inspection device uniquely arranged for detecting minute magnetic-flux anomalies which are indicative of metal defects such as cracks, pits, holes and the like. In contrast, however, to the prior-art high-intensity electromagnetizers typically having cores of minimum magnetic reluctance, the unique pipe-inspection apparatus of the present invention instead employs an electromagnetizer having a core of a substantial length and minimum cross-sectional area to specifically make its reluctance relatively large in relation to the combined magnetic reluctances of the magnetized piping wall and the annular clearances between the piping wall and the magnetizer pole pieces. In this manner, changes in either the surface conditions of the piping wall or in the internal diameter of the well bore piping will have little or no influence on the resulting flux-leakage measurements. Moreover, as a further significant aspect of the present invention, since the magnetic field produced by the magnetizer is relatively weak, other flaw-detection measurements provided by this new and improved inspection apparatus will be relatively unaffected.

14 Claims, 3 Drawing Figures

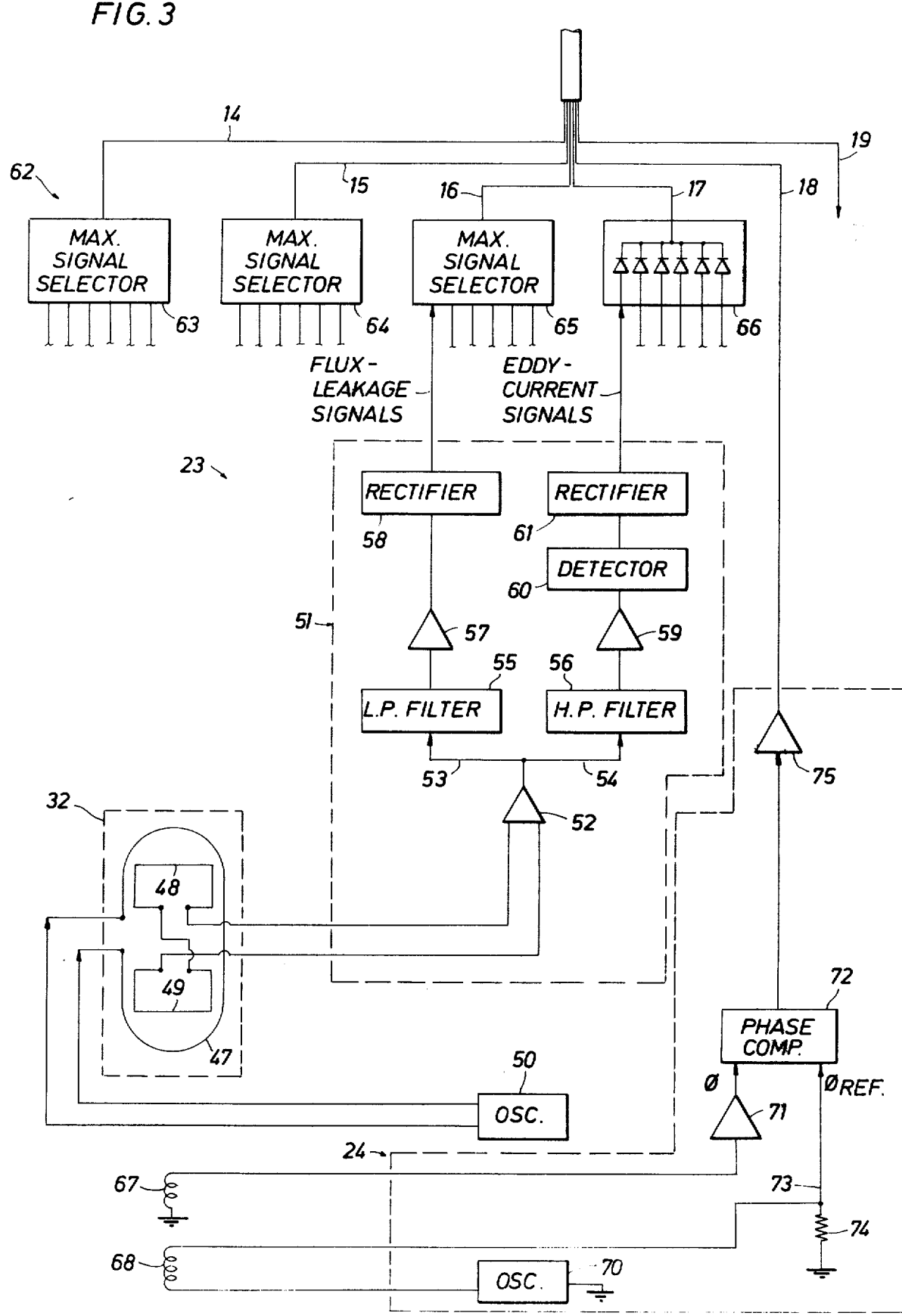

COMBINED EDDY CURRENT AND LEAKAGE FIELD DETECTOR FOR WELL BORE PIPING USING A UNIQUE MAGNETIZER CORE STRUCTURE

There have, of course, been many proposals advanced heretofore for arranging equipment to perform in situ internal inspections of oilfield piping, such as the casing commonly used for lining the walls of typical well bores, for reliably locating anomalies or defects which may, in time, potentially cause an unexpected failure of the piping. Those skilled in the art will recognize that if defects such as cracks, internal flaws, thickness reductions, unwanted holes and the like can be reliably located in advance, appropriate remedial actions can be taken to correct these potential problems before the development of some serious condition or dangerous situation.

In general, experience has shown heretofore that the most-successful defect-locating tools utilize one or more electromagnetic techniques such as measuring magnetic flux-leakages, eddy currents, or changes in a locally-induced electromagnetic field which are attributable to anomalies in the adjacent piping or casing wall. Typically, each of these recognized techniques is particularly effective for determining the location or nature of certain types of defects but is, at best, less than satisfactory in the detection of other types of common defects. For example, a well-arranged flux-leakage inspection device will ordinarily detect anomalies located at any lateral position along the thickness of a pipe wall. Conversely, since an eddy-current device is generally limited to locating defects at or near the immediately-adjacent surface, this technique is useful for inspecting only the internal wall surface of a well casing. Neither of these techniques will, however, clearly reveal a widespread reduction in wall thickness. On the other hand, typical induction-type thickness-measuring tools provide measurements which are only indicative of the overall or average wall thickness of the entire circumference of an incremental length of casing without reference either to the specific angular location of a given thin spot or to whether a reduction in the normal thickness is on the exterior or the interior of the piping.

Accordingly, it is recognized that a complete pipe-inspection survey must include two or more of these typical inspection techniques if most, if not all, types of the most-common casing defects are to be located. Moreover, since the aforementioned flux-leakage tests are particularly valuable in locating defects at any depth in a pipe wall, it is generally preferred that a thorough casing inspection survey include a flux-leakage test. Nevertheless, experience has shown that many of the present-day flux-leakage inspection tools are not fully reliable and, in most instances, will not clearly distinguish a small but possibly serious defect from the usual background noises.

One typical problem which has been frequently encountered with the prior-art flux-leakage inspection tools is that significant deposits of scale and rust on the internal walls of a string of well casing will ordinarily seriously impair the response of the inspection tool. Similarly, these prior-art flux-leakage tools has been found to be unduly affected by changes in the radial spacing or annular clearance between the internal wall of the well casing and the body of the inspection tool. Changes such as these are, of course, commonly experienced as the inspection tool moves from one joint of casing having a given "weight" or nominal wall thickness to another casing joint with a thinner or thicker nominal weight or wall thickness. Since casing joints of a given pipe size typically have a uniform outer diameter, the internal diameter will, of course, have to increase or decrease as necessary to provide a wall thickness of a desired dimension. Moreover, dimensional variations of a lesser degree are experienced even in casing joints which are nominally of the same weight since there is a moderate range of wall thicknesses and eccentricity allowed in the manufacturing specifications for casing. In any case, it will be appreciated that the performance of any flux-leakage inspection tool will be directly related to the ability of the tool to induce a magnetic flux of a predictable and uniform character in a casing wall.

Heretofore, it has been considered necessary to arrange the magnetizers of flux-leakage inspection tools to develop a sufficient magnetic flux for at least substantially saturating the adjacent portions of a well casing that is being inspected. Accordingly, these prior-art flux-leakage tools have customarily employed massive magnetizers having minimum-reluctance cores which, of necessity, are as short as possible and have pole pieces and cores of the largest-possible diameter. As a result, these prior-art tools are unduly affected by scale and rust deposits on the internal walls of a casing string as well as by even minor variations in the internal diameters of different casing joints in a given string. Moreover, where a combined casing-inspection tool includes one of these prior-art flux-leakage units as well as either an eddy-current detecting unit or an induction-type thickness-measuring unit, it has also been found that the high-intensity magnetic flux developed by the flux-leakage unit will adversely influence or totally mask the measurements provided by either of these other inspection units. This effect is particularly serious where two or more measurements are obtained with a combination tool; but difficulties of this nature have been observed even where these measurements are made at different times.

Accordingly, it is an object of the present invention to provide new and improved pipe-inspection apparatus that is particularly adapted for reliably locating magnetic anomalies or metal defects which may be present in the wall of a length of piping such as a string of well bore casing.

This and other objects of the present invention are attained by arranging a new and improved flaw-detecting inspection tool to include one or more flux-leakage detectors for surveying selected incremental portions of an adjacent pipe wall and pipe-magnetizing means for selectively subjecting those wall portions to a reduced-intensity magnetic flux which is of a low magnitude specifically selected to not even approach magnetic saturation of the pipe wall. By selectively arranging the reluctance of the pipe-magnetizing means to be substantially large in relation to the summation of the magnetic reluctance of the incremental pipe wall portions and the magnetic reluctance of the lateral clearance gaps between the pipe wall and the poles of the magnetizing means, the new and improved pipe-inspection tool of the present invention will be relatively unaffected by dimensional variations of the pipe strings it is inspecting; and any other electromagnetic inspection devices which may also be included with the pipe-inspection tool will be relatively unaffected by the concurrent operation of the flux-leakage inspection device.

The novel features of the present invention are set forth with particularity in the appended claims. The invention, together with further objects and advantages thereof, may be best understood by way of the following description of exemplary apparatus employing the principles of the invention as illustrated in the accompanying drawings, in which:

FIG. 3 is a block diagram of a preferred embodiment of electronic circuitry for the new and improved inspection tool illustrated in FIG. 1.

Figure 1:
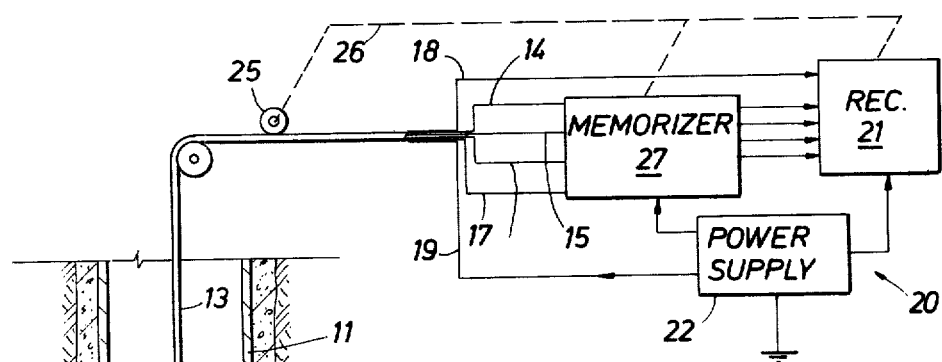
FIG. 1 is a somewhat-schematic representation of a preferred embodiment of a new and improved pipe-inspection tool arranged in accordance with the principles of the present invention as this tool will appear while operating in a typical cased well bore.

Turning now to FIG. 1, a preferred embodiment of a new and improved pipe-inspection tool 10 incorporating the principles of the present invention is schematically shown as it will appear during the course of a typical inspection operation of a length of well piping such as a string of well casing 11 which is ordinarily employed for lining the wall of a well bore 12. As depicted, the new and improved inspection tool 10 is suspended from a length of typical multi-conductor logging cable 13 which is spooled in the usual fashion on a winch (not shown) that is positioned at the surface and adapted for reeling and unreeling the cable as required for selectively moving the inspection tool through the casing 11. The several conductors 14–19 in the cable 13 are operatively connected by way of typical surface circuitry 20 for recording the several output signals from the inspection tool 10 on a galvonometer-type or CRT recorder 21 as well as for supplying power from a power supply 22 to electronic circuitry, as at 23 and 24, in the tool.

As is typical, a measuring wheel 25 arranged to be driven by movement of the cable 13 onto and off of the cable winch is cooperatively coupled, as by a pulse generator or suitable mechanical linkage 26, to the recorder 21 for producing records thereon which are a function of the depth of the tool 10 in the well bore 12. Since it is generally preferred that the several logging records provided by the recorder 21 are all presented with a common depth scale, the circuitry 20 is arranged to also include a so-called "depth memorizer" 27 which is driven by the measuring wheel 25 for momentarily storing one set of data signals from the tool 10 for simultaneous presentation on the recorder with one or more other sets of data signals from the tool. Suitable memorizer circuits are shown in U.S. Pat. No. 3,166,709 and U.S. Pat. No. 3,405,349 which are respectively incorporated by reference herein.

As illustrated, the new and improved inspection tool 10 includes an elongated body 28 having one or more typical tool centralizers, as at 29 and 30, which are cooperatively mounted on upper and lower portions thereof for retaining the tool in a substantially-coaxial relationship within the well casing 11. In general, the depicted preferred embodiment of the new and improved tool 10 is comprised of a flaw-detection unit 31 having a plurality of casing-engaging inspection shoes, as at 32 and 33, which are cooperatively arranged around casing-magnetizing means 34 and operatively connected to the electronic circuitry 23 enclosed in the upper portion of the tool body 28. The preferred embodiment of the new and improved inspection tool 10 also includes an induction-type thickness-measuring unit 35 which is dependently suspended from the body 28 and operatively connected to the electronic circuitry 24 enclosed in the lower portion of the tool body.

Accordingly, as will subsequently be explained in greater detail, as the new and improved tool 10 is moved through the casing 11 the several casing-condition signals respectively provided by the flaw-detection unit 31 and the thickness-measuring unit 35 will be successively displayed or presented on the surface recorder 21 as a function of the successive depth locations of the tool. As previously mentioned, it is preferred that the surface circuitry 20 includes a memorizer 27 so that the casing-condition signals respectively provided by the flaw-detection unit 31 and the thickness-measuring unit 35 will be displayed or presented on the recorder 21 on a common depth scale for facilitating the subsequent interpretation of the resulting log record.

It is, of course, well known that when an incremental length of ferromagnetic or paramagnetic piping, such as the well casing 11, is subjected to a longitudinally-oriented DC magnetic field, generally-longitudinal lines of magnetic flux will be established in the casing wall. So long as the magnetized portion of the casing wall is magnetically homogenuous, these longitudinally-oriented flux lines will essentially remain within the wall of the casing 11 and will be relatively uniform in density. On the other hand, should there be a magnetically-responsive anomaly or defect such as a crack, a pit, an opening or the like in the magnetized portion of the casing 11, the flux lines will be correspondingly distorted around this defect to produce a detectable so-called "flux-leakage" pattern or anomaly on the casing wall immediately adjacent to the defect. Thus, as is well known, the movement of a suitable detecting coil along the wall of a magnetized portion of the casing 11 will be effective for inducing representative voltage signals in the coil as it passes through one of these flux-leakage patterns. It is, of course, recognized that, for a given situation, the magnitude of these output signals will be directly related to the size of the magnetically-responsive piping anomaly.

Accordingly, the several wall-engaging inspection shoes 32 and 33 of the flaw-detection unit 31 are respectively arranged at spaced intervals around the tool body 28 for detecting flaws or defects around the full circumference of the casing 11. As depicted in FIG. 1, this complete circumferential coverage is best accomplished by dividing the several inspection shoes and symmetrically arranging half of these shoes, as at 32, at equal intervals around one portion of the body 28 and symmetrically arranging the remaining shoes, as at 33, at equal intervals around a lower portion of the body. By angularly offsetting the lower shoes 33 in relation to the upper shoes 32, each of the lower shoes will be respectively examining a narrow longitudinal strip of the casing 11 which lies between and slightly overlaps two adjacent strips of the casing that are being examined by the two inspection shoes immediately there-above. In other words, as the new and improved inspection tool 10 is moved through the casing 11, the upper inspection shoes, as at 32, will be continuously examining a number of circumferentially-spaced bands or longitudinal strips along the casing wall having gaps therebetween and the lower shoes, as at 33, will be continuously examining these gaps to assure a complete survey of the casing wall.

Figure 2:
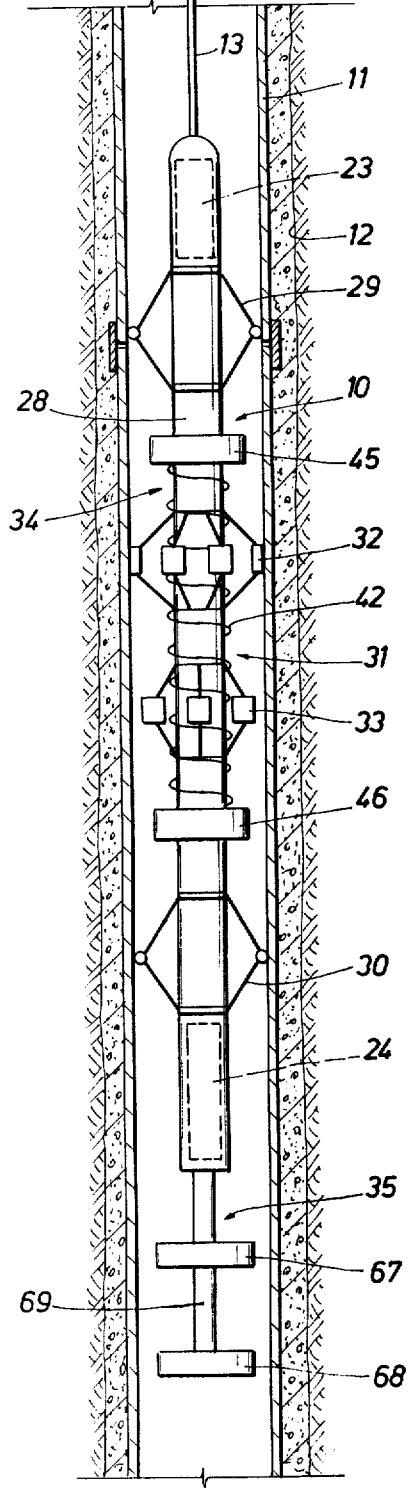
FIG. 2 depicts various constructional details of a portion of the new and improved tool of FIG. 1.
Figure 2:
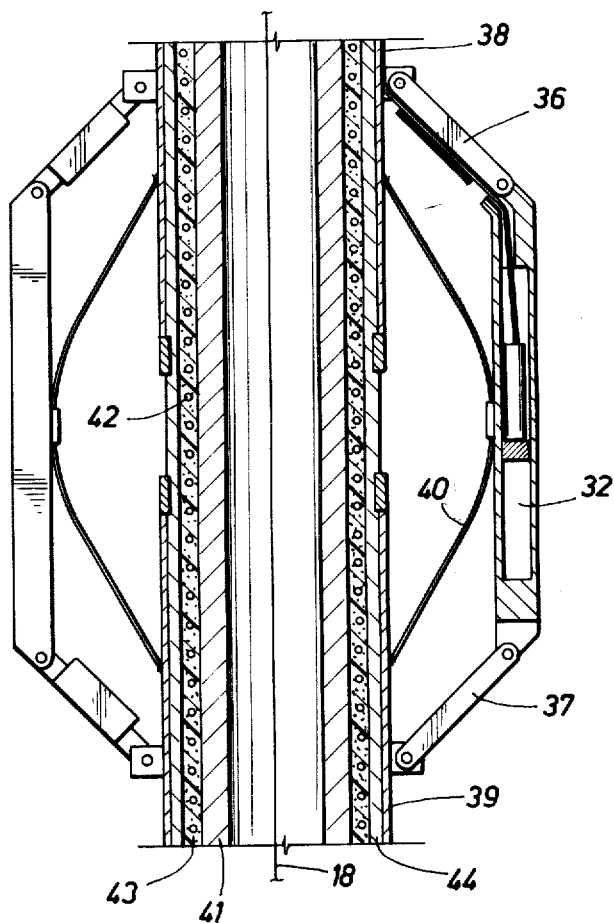

Those skilled in the art will, of course, recognize that there are a number of satisfactory mechanical arrangements which may be employed for maintaining the inspection shoes, as at 32 and 33, in operative engagement with the inner wall of the casing 11. For example, the several inspection shoes, as at 32 and 33, could be mounted on the tool body 28 in keeping with the principles of U.S. Pat. No. 2,736,967. As shown in FIG. 2, however, in the preferred embodiment of the present invention the upper and lower ends of the inspection shoes, as at 32, are pivotally coupled to the outer ends of rigid arms, as at 36 and 37, which, in turn, have their inner ends pivotally coupled to longitudinally-spaced collars, as at 38 and 39, slidably mounted around the tool body 28. Springs, as at 40, are cooperatively arranged for normally urging the outer faces of the several inspection shoes, as at 32, into sliding engagement with the wall of the casing 11. Inasmuch as the particular details of how the inspection shoes, as at 32 and 33, are mounted on the new and improved tool 10 are not pertinent to understanding the present invention it is believed that these mechanical details are adequately shown in FIG. 2.

As previously mentioned, the magnetizing means 34 of the new and improved inspection tool 10 are cooperatively arranged for establishing a longitudinally-extending DC magnetic field in that section of the casing 11 which the several inspection shoes, as at 32 and 33, are then engaged with. Accordingly, to attain the objects of the present invention, the magnetizing means 34 include an elongated paramagnetic or ferromagnetic core 41 which, as a matter of expediency, is arranged to serve as an intermediate portion of the tool body 28. In the preferred embodiment of the new and improved inspection tool 10, a magnetizing coil 42 is helically disposed around the magnetizer core 41 and cooperatively arranged to be coupled to the cable conductor 19 leading to the surface power supply 22. To isolate the coil 42 from any electrically-conductive fluids in the well bore 12, the coil is preferably enveloped or embedded in a suitable elastomeric or plastic electrical insulating material as at 43. The entire magnetizer coil 42 is also preferably covered by a thin sleeve, as at 44, of a non-magnetic metal which is suitably sized for slidably carrying the several sliding collars, as at 38 and 39, to which the inspection shoes, as at 32, are coupled. To assure the maximum effectiveness of the flaw-detection unit 31, the upper and lower inspection shoes 32 and 33 are mounted around the intermediate portion of the magnetizer coil 42 and enlarged-diameter upper and lower pole pieces 45 and 46 of a paramagnetic or ferromagnetic material are operatively coupled to the opposite ends of the magnetizer core 41.

It will be recognized, therefore, that the magnetizing means 34 will establish a longitudinally-elongated, toroidally-shaped magnetic field which is generally directed in a path extending along the axis of the central magnetizer core 41, passing between the circumferential faces of the upper and lower poles 45 and 46 and the respectively-adjacent surfaces of the casing wall, and extending through the full circumference of the incremental length of the casing 11 disposed between those spaced wall surfaces. The inspection shoes, as at 32 and 33, will, of course, always be in contact with the mid-portion of the incremental length of the casing 11 that is then being magnetized. Accordingly, for a given number of turns of the magnetizing coil 42 and applied DC current, it will be realized that the resulting flux intensity will be a function of the overall summation of the several magnetic reluctances that are then present in the above-described path of the toroidal magnetic field. Thus, the intensity or flux density of the magnetic field established by the magnetizing means 34 will be governed by the total summation of the reluctance of the incremental length of the casing 11 that is then being examined, the magnetic reluctances of the annular gaps between the casing wall and the upper and lower pole pieces, and the overall magnetic reluctance of the core 41 and the pole pieces 45 and 46.

Heretofore, in prior-art flux-leakage, flaw-detection tools of a similar nature, it has been thought more effective to approach magnetic saturation of the adjacent casing wall; and, therefore, to achieve this, it has been correspondingly necessary to minimize the magnetic reluctance of the core as far as possible. In keeping with the principles of the present invention, however, it has been found that superior operating results can be achieved by specifically arranging the magnetizing means 34 so that the magnetic reluctance of the core 41 and the pole pieces 45 and 46 is significantly large in relation to the summation of the combined magnetic reluctances of the annular gaps between the outer faces of the two pole pieces and the incremental section of the casing 11 that is then being magnetized. This will, therefore, result in the flux intensity produced by the magnetizing means 34 being relatively constant even where there are minor variations either in the magnetic reluctance of the incremental length of the casing 11 being examined or in the widths of the annular gaps between the casing wall and the upper and lower pole pieces 45 and 46. As a result, in sharp contrast with the operating characteristics of prior-art tools of this nature, the new and improved flaw-detection unit 31 will be nature, the new and improved flaw-detection unit 31 will be capable of providing a more-reliable flux-leakage inspection of well bore pipe strings such as the casing 11 without being materially affected by either minor variations in the internal diameter of the pipe string or changes in the condition of the wall surface.

It will, of course, be recognized that the deliberate and substantial increase of the magnetic reluctance of the core assembly 41 of the magnetizer means 34 can be achieved in various manners. First of all, and perhaps of most importance, it has been found that a substantial increase in the internal magnetic reluctance of the magnetizer means 34 can be attained by arranging the core 41 to have a minimum diameter so that the transverse cross-sectional metal area of the core will be no more than equal, if not substantially smaller, in relation to the transverse cross-sectional metal area of the casing 11. Moreover, the overall reluctance of the core 41 can also be substantially increased in relation to the combined magnetic reluctance of the complete toroidal path of the established magnetic field by making the core substantially longer than the cores ordinarily used heretofore with comparable prior-art tools. A further increase in the reluctance of the core 41 can be achieved by forming the core of a metal having a relatively-low magnetic permeability instead of the highly-permeable metals heretofore considered to be advantageous if not essential.

It has also been found helpful to make the vertical height of the upper and lower pole pieces 45 and 46 somewhat greater than has ordinarily been done heretofore with comparable prior-art flux-leakage inspection tools. This increased height has the dual advantage of further increasing the magnetic reluctance of the overall core assembly 41 of the magnetizer 34 as well as simultaneously minimizing the magnetic reluctance across the annular gaps between the faces of the pole pieces 45 and 46 and the inner wall surface of the casing 11.

Adoption of at least one, if not all, of these several techniques in arranging the core assembly 41 of the magnetizing means 34 has been found to provide superior and unexpected results in comparison with similar flux-leakage tools of the prior-art. Since the particular dimensions to be employed for a given inspection tool incorporating the principles of the present invention are, of course, solely dependent on the particular range of pipe sizes that the tool will be designed for, it is believed more appropriate to describe the design parameters for the new and improved tool 10 in terms of preferred ratios of the magnetic reluctance for the core assembly 41 of the magnetizer 34 to the reluctance of the annular gaps around the pole pieces 45 and 46 and the reluctance of typical oilfield piping such as the casing 11.

As previously mentioned, the magnetic path or toroidal loop involved with the magnetizer 34 is a series magnetic circuit consisting of the core 41, the two annular spaces around the upper and lower pole pieces 45 and 46, and the incremental length of the casing 11 that is then being magnetized. Expressing this loop mathematically, the following equation may be considered:

$$\frac{NI}{\Phi} = \frac{L_c}{A_c \mu_c} + \frac{2t_g}{A_g \mu_g} + \frac{L_p}{A_p \mu_p} \qquad \text{(Eq. 1)}$$

where, $N$ = number of turns of the magnetizer coil 42;
$I$ = current flow in the magnetizer coil 42;
$\Phi$ = magnetic flux in the magnetic circuit;
$L_c$ = overall length of the core 41 and the pole pieces 45 and 46;
$A_c$ = transverse cross-sectional metal area of the core 41;
$\mu_c$ = relative magnetic permeability of the core 41;
$t_g$ = width or thickness of the annular gap or space between either of the pole pieces 45 and 46 and the inner wall of the casing 11;
$A_g$ = face area of either of the pole pieces 45 and 46 (i.e., height × circumference);
$\mu_g$ = relative magnetic permeability of well fluids in the annular gaps (ordinarily = 1.0);
$L_p$ = length of incremental section of the casing 11 being inspected ($L_c = L_p$);
$A_p$ = transverse cross-sectional metal area of the casing 11; and
$\mu_p$ = relative magnetic permeability of the casing 11.

Accordingly, in contrast to the usual prior-art practice (such as discussed in U.S. Pat. No. 3,543,144) where magnetic saturation of the casing is ordinarily approached and the first term in the above equation is specifically made as small as possible, it is essential in the present invention to make this first term as large as practical in relation to the other two terms in the equation. As previously discussed, it is important to make $L_c$ relatively large; but, even more so, to make $A_c$ and $\mu_c$ small in relation to $A_p$ and $\mu_p$ respectively.

As a typical example of the significance of these relationships, it will be recognized that to make the first term of Equation 1 greater than the third term, the diameter of the core 41 must be relatively small so that the cross-sectional metal area of the core will be no more and, if at all possible, much less than the cross-sectional metal area of the well pipe that is being inspected. Similarly, the relative magnetic permeability of the core 41 should be as low as practical in relation to that of the pipe and, from a practical standpoint, should be no higher.

Assuming, for example, a typical 5-inch casing with an average wall thickness of ¼-inch and a typical relative magnetic permeability of 100, the third term in Equation 1 will be approximately $0.00255L_p$. Thus, it can be shown that if a metal having a relative permeability of 100 is used for the core 41, if it were solid the core could have a diameter no larger than something slightly more than 2-inches if the first and third terms of Equation 1 are to be even equal. Accordingly, in the present invention, it is preferred to form the core 41 of metals such as various hard steels having relative magnetic permeabilities in the order of no more than about 40 or 50 and to limit the outer diameter of the core to something in the order of one-half, or preferably considerably less, of the internal diameter of the piping being inspected so that the magnitude of the first term in Equation 1 is at least somewhat greater, if not significantly greater, than the magnitude of the third term in the equation. Since wires must be extended through the body 28 to the thickness-measuring unit 35, it will, of course, be advantageous to provide an axial passage through the core 41 which will further reduce its cross-sectional metal area. By way of example, to arrange the tool 10 for inspecting the aforementioned 5-inch casing, the magnetizer core 41 could readily be designed so that the first term in the equation would be in the order of $0.0085L_c$ or somewhat more than three times the magnitude of the third term.

It will, of course, be seen that by making the first term of Equation 1 substantially larger than the third term, the second term will become almost insignificant in relation to the first term. For example, in the exemplary situation described above, it is quite easy with presently-available metals to make the first term of Equation 1 at least 40 or 50 times greater than the second term. Thus, with such large relative differences, it can be readily shown that major changes such as ⅛-inch or even more in the width of the annular gaps between the wall of the casing 11 and the pole pieces 45 and 46 will affect the overall reluctance of the magnetic circuit of the magnetizer 34 by no more than about 1 to 2 percent. Those skilled in the art will, of course, appreciate that similar flux-leakage inspection tools of the prior art will inherently experience far greater changes in the overall reluctance of their magnetizing circuits when there is a change in the gaps around the poles of their magnetizer of even as little as 1/16-inch.

The significance of these minute changes in the overall reluctance of the magnetic circuit of the magnetizer 34 caused by significant variations in the width of the annular gaps between the casing 11 and the pole pieces 45 and 46 becomes even more apparent when it becomes necessary to distinguish a signal caused by a casing defect from a signal caused by either a harmless coating of scale on the casing wall or a normal diametrical variation from one casing joint to another. For instance, as the new and improved inspection tool 10 is passed through a length of well bore piping, such as the casing 11, there will always be minor ripples or variations in the output signal which may be characterized as "magnetic noise." These noise signals will, of course, be originated by such things as wobble or "chattering" of the inspection shoes 32 and 33 as well as by the minute changes in the annular gaps around the pole pieces 45 and 46 due to pipe roughness and scale coatings on the pipe wall. As discussed above, however, these noise signals will be minor due to the unique design of the new and improved flaw-detection unit 31. Accordingly, when a flux anomaly caused by a piping defect is traversed by one of the inspection shoes, as at 32 and 33, the resulting output signal will be of significantly-greater amplitude than the background level of continuous magnetic noise signals and, therefore, will be readily distinguishable on the logging record provided by the recorder 21. In other words, the signal-to-noise ratio of the new and improved flaw-detection unit 31 has been found to be exceptionally favorable in field operations.

On the other hand, with prior-art tools (such as that shown in U.S. Pat. No. 3,543,144) where even a minor change in the annular gaps between the pole pieces and the piping wall will significantly change the overall magnetic reluctance of the magnetizing circuit, it has been noted that the output signals from such tools are ordinarily extremely noisy. Thus, in the use of such prior-art tools, it has been frequently demonstrated that it is often difficult, if not impossible, to distinguish flux-leakage signals caused by minor pipe defects from the ordinary and high-magnitude noise or background signals. In comparison, the unique arrangement of the magnetizer 34 of the new and improved inspection tool 10 has, for all practical purposes, eliminated any significant effects on the operation of the tool which would otherwise occur upon movement of the tool either through adjoining pipe joints of slightly different internal diameters or through particularly rough or scale-coated pipes.

The preceding discussion has, of course, to this point been directed to the design of the magnetizing means 34 to allow a flux-leakage inspection to be performed by the flaw-detection unit 31. It is, however, preferred to also conduct an eddy-current inspection with the flaw-detection unit 31 for distinguishing piping defects on or near the inner surface of the well bore piping from defects which may be either on the exterior of the piping or at some depth in the piping wall. As best seen in FIG. 3, this is best accomplished by operatively combining the flux-leakage and eddy-current measurements in the flaw-detection unit 31.

Accordingly, as schematically represented in FIG. 3, the flaw-detection unit 31 of the new and improved tool 10 is preferably arranged so that the several inspection shoes, as at 32, will each carry an eddy-current oscillator coil 47 and two differentially-connected detecting coils 48 and 49. To induce eddy currents in the adjacent wall surface of the well bore pipe being examined, the oscillator coils, as at 47, in each of the several inspection shoes, as at 32, are respectively coupled to a common high-frequency oscillator 50 in the downhole circuitry 23. On the other hand, the detecting coils 48 and 49 in each of the several inspection shoes, as at 32, are respectively coupled to an individual signal-separating circuit, as at 51, which is cooperatively arranged for providing separate output signals respectively representative of the eddy-current measurements and the flux-leakage measurements obtained by each particular inspection shoe. Since the signal-separating circuits, as at 51, for each of the several inspection shoes, as at 32, are preferably identical to one another, only one of these several circuits included in the downhole circuitry 23 are shown in FIG. 3.

As illustrated, the combined signals respectively representative of the eddy-current measurements and the flux-leakage measurements are applied to the input terminals of a typical wide-band amplifier 52 included in the signal-separating circuit 51. The output signals from the amplifier 52 are then divided into two channels, as at 53 and 54, and respectively coupled to a typical low-pass filter 55 and a typical high-pass filter 56 which are cooperatively designed to accept signals respectively representative of typical low-frequency flux-leakage signals and typical high-frequency eddy-current signals. The low-frequency or flux-leakage channel 53 of the signal-separating circuit 51 includes a typical amplifier 57 and a rectifier 58 for providing an unfiltered output signal with pulses or peaks of a selected polarity each time the inspection shoe 32 senses a piping defect. The amplitude of the output pulses from the flux-leakage channel 53 of the signal-separating circuit 51 will, of course, be proportional to the severity or extensiveness of the detected defect. In a similar fashion, the eddy-current channel 54 of the signal-separating circuit 51 is provided with an amplifier 59 and a detector 60 and a rectifier 61 for converting the high-frequency defect signals to pulses or peaks of a selected polarity each time the inspection shoe 32 senses a defect in the piping which is either on or very near the inner piping wall. Hereagain, the amplitude of these output pulses will be proportional to the severity of the defect detected by the eddy-current inspection.

It will, of course, be appreciated that the overall purpose of the new and improved flaw-detection unit 31 is to locate piping defects of a potentially-serious nature. Thus, it is only academic whether there is more than one defect in a given circumferential section of a well pipe; and the practical question is simply whether or not there is a defect in a given incremental length of piping and, if so, how severe is it. Accordingly, in the new and improved flaw-detection unit 31, circuit means 62 are provided in the downhole circuitry 23 for differentiating between the several output signals which may be simultaneously supplied from one or more of the inspection shoes, as at 32, and providing only a single output signal which is representative of the most-severe defect which is then being sensed by those inspection shoes. In the preferred embodiment of downhole circuitry 23 used in the present invention as depicted in FIG. 3, the signal-differentiating circuit means 62 include a number of diode arrays 63-66 that are arranged as OR gates and adapted for respectively differentiating the flux-leakage signals as well as the eddy-current signals from the upper and lower inspection shoes, as at 32 and 33. Thus, as illustrated, the eddy-current output signal from each of the signal-separating circuits, as at 51, respectively associated with each of the upper inspection shoes, as at 32, are respectively coupled to the several inputs of the maximum-signal selector 66.

Accordingly, an eddy-current output signal from any one of the several upper inspection shoes, as at 32, will be supplied to the cable conductor 17 by the signal-separating circuit 51 and maximum-signal selector 66. Thus, should there be two or more eddy-current signals which are simultaneously applied to the signal-selecting circuit 66, only the greatest of these several input signals from the upper shoes, as at 32, will be supplied at any given moment to the cable conductor 17. The other signal-selecting circuits are similarly arranged, with the circuit 63 preferably being coupled to the conductor 14 for passing only the largest flux-leakage signal from the several lower inspection shoes, as at 33, and the circuit 64 being arranged to differentiate between the largest eddy-current signal from the lower shoes. The signal-selecting circuit 65 similarly distinguishes the largest flux-leakage signal from the upper inspection shoes, as at 32.

Referring again to FIG. 1, the thickness-measuring unit 35 is comprised of a pair of induction coils 67 and 68 which are coaxially wound around an elongated non-magnetic mandrel 69 dependently coupled to the tool body 28 and longitudinally separated from each other by a distance which is greater than the diameter of the casing 11. Although other types of inductive thickness-measuring devices can, of course, be employed with the new and improved inspection tool 10, it has been found that an arrangement such as described in U.S. Pat. No. 2,573,799 is entirely satisfactory for attaining the objects of the present invention.

Accordingly, as schematically depicted in FIG. 3, the electronic circuitry 24 employed with the preferred embodiment of the thickness-measuring unit 35 includes an oscillator 70 that is coupled to one end of the induction coil 68 for establishing an alternating magnetic field in the adjacent casing wall which is detected by the other coil 67. As described in the aforementioned patent, by virtue of the longitudinal spacing between the coils the phase of the output signal from the detector coil 67 in relation to the oscillator signal supplied to the exciter coil 68 is representative of the volume of the metal contained in the incremental length of the casing 11 then lying between the two coils. Since the longitudinal spacing between the coils 67 and 68 is fixed, this means, therefore, that a phase relationship between the input and output signals is a function of the average overall wall thickness of that incremental length of the casing 11. To determine this phase relationship, the output signal from the detector coil 67 is coupled by way of an amplifier 71 to one input of a typical phase comparator 72. To provide a reference signal to the comparator 72, the phase of the current in the exciter coil 68 is sensed, as at 73, by coupling the other input of the phase comparator to the ungrounded end of a resistor 74 connected to the opposite end of the exciter coil. The output of the phase comparator 72 is, in turn, coupled to the cable conductor 18 by way of an amplifier 75 included in the downhole circuitry 24.

Accordingly, it will be recognized that with the new and improved inspection tool 10 arranged as illustrated in the several drawings, a comprehensive inspection will be conducted as the tool is traversed through a string of well bore piping such as the casing 11. Although this inspection can, of course, be accomplished as the tool 10 is lowered through the casing string 11, it is preferred that the survey be taken as the inspection tool is being raised in the well bore 12 so that the cable 13 will be uniformly tensioned to provide more-reliable depth measurements for the recorder 21.

As the new and improved inspection tool 10 is being operated to survey at least one or more intervals of the casing string 11, it will, of course, be appreciated that the recorder 21 will be simultaneously producing five separate log traces which are individually, as well as collectively, representative of the present condition of the casing. These log traces are, of course, displayed on a common depth scale by virtue of the memorizer 27. Four of these logs are, of course, the eddy-current and the flux-leakage inspection measurements respectively obtained by the upper and lower shoes, as at 32 and 33, of the flaw-detection unit 31, with the fifth log trace being the average wall-thickness measurements provided by the thickness-measuring unit 35.

Those skilled in the art will, of course, recognize that although there have been various proposals advanced heretofore for combining various defect measurements, there has yet been no commercially-acceptable defect-inspection tool which satisfactorily combines eddy-current and flux-leakage measurements for surveying well bore piping such as the casing string 11. As will subsequently be explained, however, it has been found that the new and improved inspection tool 10 of the present invention is particularly successful in obtaining multiple defect measurements such as the flux-leakage signals, the eddy-current-signals, and the average thickness signals provided by the tool.

To appreciate the significant role that the design of the magnetizer 34 plays in allowing the new and improved inspection tool 10 to also obtain reliable thickness measurements, it will be recalled from the previous discussion that the magnetizer is arranged for producing a magnetic field of a relatively-low order of magnitude as well as of a substantially-constant flux density. The significance of the low intensity and constant flux density of this magnetic field is best understood when it is recognized that for a given frequency of the oscillator 70, the phase-relationship measurements provided by the thickness-measurement unit 35 are determined by the thickness, the electrical resistivity, and the magnetic permeability of the incremental length of the casing 11 then being inspected. However, it is well known that the permeability of a ferromagnetic or paramagnetic metal is materially dependent upon the intensity of any magnetic field which is then established in this metal as well as upon the previous magnetic history of that metal. Variations in either the present magnetic state or the average thickness of an incremental length of well piping will, therefore, respectively produce corresponding variations in the phase relationships measured by the thickness-measurement unit 35.

Accordingly, it will be appreciated that since the unique design of the magnetizer 34 induces a relatively-constant magnetic flux density in the casing 11, as the new and improved inspection tool 10 is passed therethrough the thickness-measuring unit 35 will, for all practical purposes, be responsive only to changes in the average wall thicknesses of the incremental lengths of casing which are being successively inspected. It should also be recognized that by virtue of the relatively-low flux density produced by the magnetizer 34, there will be little or no residual magnetism left in the casing 11 after the magnetizer is moved. Thus, as the trailing thickness-measuring unit 35 is passed through a given incremental length of the casing string 11, the phasedifference measurements provided by the phase comparator 72 will be substantially, if not altogether, unaffected by any permeability changes in the casing that would have been otherwise produced by the residual magnetism that will inherently be created by the high-saturation magnetizers used in prior-art tools.

Those skilled in the art will, of course, recognize that the subsequent magnetic state of a ferromagnetic material that has been highly magnetized previously will be totally unpredictable. As a result, where a series of thickness-measurements are made with a tool such as the thickness-measuring unit 35 in a casing, as at 11, having a substantial degree of residual magnetism, the resulting measurements will be affected by both the metal thickness and the present magnetic permeability of the casing string. If it can be reasonably assumed that, during a given thickness-measurement run, the magnetic state of the casing string, as at 11, is relatively constant, the resulting thickness measurements will, of course, be at least reasonably indicative of thickness variations along the casing string. On the other hand, a subsequent thickness-measurement run through the same casing string, as at 11, cannot be safely correlated with prior runs since it is totally unpredictable as to what effect the present magnetic state of the casing string is having on the accuracy of the new thickness measurements. This is true regardless of whether or not the casing string, as at 11, is again remagnetized with a strong magnetic field. Accordingly, it will be seen that in addition to the benefits of a constant magnetic flux density, the unique magnetizer 34 will induce such a weak magnetic field in the casing 11 that there will be little or no residual magnetism left in the casing to affect either the present thickness measurements or those obtained in the same string at a later date.

Similarly, the uniform flux density and relatively-weak intensity of the magnetic fields successively induced in the well casing 11 by the magnetizer 34 have also been found to be very significant in obtaining reliable eddy-current measurements in typical strings of well casing. By way of explanation, it is, of course, recognized that the reliability and, therefore, the effectiveness, of an eddy-current measurement is directly related to the relative magnetic permeability of the paramagnetic or ferromagnetic metal that is being inspected. Moreover, it can be shown that as the relative magnetic permeability of a given magnetic material is increased, the depth of examination or penetration will be proportionally decreased. Accordingly, it has been found by experimentation that the effectiveness of an eddy-current measurement of a given casing wall will be substantially impaired, if not altogether nullified, by the presence of a external magnetic field which either varies significantly in strength or substantially approaches magnetic saturation of the adjacent casing wall.

As previously discussed, however, it will be recognized that the unique design of the magnetizer 34 maintains a substantially-constant and relatively-weak magnetic field in the casing string 11 as the new and improved inspection tool 10 is conducting an inspection operation. Thus, as several inspection shoes, as at 32 and 33, are respectively traversed along the inner wall of the casing string 11, the previously-described flux-leakage measurements and eddy-current measurements can be simultaneously obtained without undue interference to the latter measurement by the low-level and constant magnetic field established by the magnetizer 34. Similarly, although the magnetizer 34 will progressively induce a magnetic field in the incremental lengths of the casing string 11 which are being successively surveyed by the flaw-detection unit 31, the measurements provided by the trailing thickness-measuring unit 35 will be affected little, if any, by any low-level residual magnetism which may be present in the casing wall as the thickness-measuring unit subsequently moves through those portions of the casing.

Accordingly, the combined logging record provided by the recording apparatus 21 will represent three basic records indicative of the present physical condition of the casing string 11 at each depth interval surveyed by the new and improved inspection tool 10. One of these basic records will, of course, be the flux-leakage measurements which are respectively representative of the presence and relative severity of the worst defect around the circumference of a given incremental length of the casing string 11. These flux-leakage measurements will, of course, be relatively inconclusive as to whether a detected defect is exterior of the casing 11, or is an internal defect within the casing wall, or is on the interior surface of the casing. However, since the eddy-current inspection is, for all practical purposes, only effective for locating defects which are either on the internal surface of the casing 11 or very near this surface, it will be appreciated that the simultaneous appearance of defect signals on both the flux-leakage logging trace and the eddy-current logging trace will ordinarily indicate that the detected defect is on or very near the interal surface of the casing. Conversely, it will be recognized that a defect signal at a given depth which is present only on the flux-leakage logging trace will be indicative that the detected defect is either on the exterior of the casing 11 or is at a considerable depth inside the casing wall itself. It should be noted, of course, that by virtue of the several maximum-signal selector circuits 63–66 the simultaneous indication of defects on the flux-leakage and eddy-current logging records will generally be caused by the same defect.

Although the relative amplitudes of the defect signals produced on the flux-leakage and eddy-current logs will be somewhat representative of the severity of a detected defect, it will, of course, be appreciated that these defect signals are essentially only qualitative in nature. Accordingly, to obtain a more-quantitative measurement of the severity of a given defect, the thickness-measuring logging record must be consulted. Thus, since this measurement is indicative of the overall average wall thickness of a given incremental length of the casing 11, the thickness measurement provides a general indication of the severity of any detected casing defect. It should be noted that the presence of a defect signal on only the defect-measuring logging records from, for example, the upper shoes, as at 32, will typically indicate that the detected defect does not extend too far in a lateral or circumferential direction since the lower shoes, as at 33, failed to detect it. Thus, a significant reduction in the average wall-thickness at this depth interval will generally indicate an extremely-severe, localized defect. On the other hand, the simultaneous appearance of the defect signals of different amplitudes on the logging record from the upper and lower shoes 32 and 33 will orginarily indicate some degree of circumferential extent of the detected defect. Conversely, uniform defect signals on the logging records from the upper and lower shoes 32 and 33 will most likely indicate a substantially-uniform circumferential defect. The severity or depth of these several types of defects can, of course, be generally estimated from the thickness-measuring logging record.

Accordingly, it will be recognized that the present invention has provided new and improved pipe-inspection apparatus which is particularly adapted for locating defects in well bore piping such as casing strings by means of flux-leakage measurements. By arranging a pipe magnetizer to include a high-reluctance core, the magnetic field which will be established in the adjacent piping wall will be of such low intensity that magnetic saturation of the adjacent metal will not even be approached. Moreover, by virtue of this high-reluctance magnetizer core, significant changes in either the internal diameter of the piping string or the condition of the interior surface of the piping will have little or no effect on the flux density of the substantially-constant magnetic field. Accordingly, since there will be a substantially-constant magnetic field established in the piping string, the magnetic permeability of the piping will remain relatively constant and eddy-current and thickness measurements obtained along with the flux-leakage measurements will be significantly more accurate.

While only a particular embodiment of the present invention has been shown and described, it is apparent that changes and modifications may be made without departing from this invention in its broader aspects; and, therefore, the aim in the appended claims is to cover all such changes and modifications as fall within the true spirit and scope of this invention.

What is claimed is:

1. Pipe-inspection apparatus adapted for locating magnetically-anomalous defects in or on either the interior or exterior walls of a string of well-bore piping having a known minimum internal diameter, a known relative magnetic permeability and a known transverse cross-sectional metal area, and comprising:

an elongated body adapted for suspension in such a piping string from a well-logging cable and including upper and lower longitudinally-spaced pole pieces respectively having a maximum outer diameter somewhat less than said known internal piping diameter and magnetically coupled to the opposite ends of an elongated reduced-diameter core member of a magnetic metal having a relative magnetic permeability no greater than said known piping permeability and a transverse cross-sectional metal area less than said known piping metal area;

flux-inducing means adapted for establishing a longitudinally-oriented unidirectional magnetic flux along an incremental portion of such well-bore piping located between said upper and lower pole pieces and including a magnetizing coil coaxially wound around said core member;

eddy-current inducing means adapted for establishing eddy currents along and adjacent to the interior wall of said incremental piping portion and including an electrical oscillator, and a plurality of output coils respectively coupled to said oscillator and cooperatively arranged at circumferentially-spaced intervals around said core member for being operatively positioned immediately adjacent to said interior wall to induce eddy currents therein;

defect-sensing means including a plurality of differentially-wound pairs of detecting coils cooperatively arranged at circumferentially-spaced intervals around said core member for being operatively positioned immediately adjacent to said interior wall to simultaneously detect flux-leakage variations as well as eddy-current variations appearing thereon and caused by magnetically-anomalous defects in said incremental piping portion during the movement of said detecting coils therethrough; and defect-responsive circuit means operatively coupled to said detecting coils and cooperatively arranged for providing first and second output signals in response to said flux-leakage variations and said eddy-current variations respectively.

2. The pipe-inspection apparatus of claim 1 wherein each of said output coils is cooperatively arranged in a wall-engaging inspection shoe along with a respective pair of said detecting coils.

3. The pipe-inspection apparatus of claim 1 wherein the arithmetical product of said cross-sectional metal area and relative magnetic permeability of said core member is at least twice the arithmetical product of said known piping metal area and piping permeability.

4. The pipe-inspection apparatus of claim 1 wherein said relative magnetic permeability of said core member is no more than about half of said known piping permeability.

5. The pipe-inspection apparatus of claim 1 further including:

a well-logging cable connected to said body and cooperatively arranged for moving said body between selected depth intervals in such a piping string; and recording means coupled to said cable and cooperatively arranged for individually recording said first and second output signals as a function of the depth interval at which said output signals are obtained.

6. The pipe-inspection apparatus of claim 5 wherein said defect-responsive circuit means are disposed within said body.

7. The pipe-inspection apparatus of claim 1 wherein said defect-responsive circuit means further include first and second signal-differentiating means cooperatively coupled to each of said detecting coils and operatively arranged for providing said first and second output signals as a function of only the greatest ones of said flux-leakage variations and eddy-current variations respectively which are simultaneously detected at any given time by two or more of said detecting coils.

8. The pipe-inspection apparatus of claim 7 further including:

a well-logging cable connected to said body and cooperatively arranged for moving said body between selected depth intervals in such a piping string; and recording means coupled to said cable and cooperatively arranged for individually recording said first and second output signals as a function of the depth interval at which said output signals are obtained.

9. The pipe-inspection apparatus of claim 8 wherein said defect-responsive circuit means are disposed within said body.

10. The pipe-inspection apparatus of claim 1 further including:

an elongated non-magnetic member tandemly coupled to said body;

first and second induction coils coaxially wound around said non-magnetic member and longitudinally separated by a distance greater than said known internal piping diameter;

oscillator means cooperatively coupled to said first induction coil for inducing a voltage in said second induction coil having a phase relationship with respect to the output of said oscillator means which varies in proportion to the average wall thickness of said incremental piping portion disposed in the induction field between said induction coils; and thickness-measuring circuit means cooperatively coupled to said induction coils for measuring variations in said phase relationship to provide additional output signals representative of said average wall thickness.

11. The pipe-inspection apparatus of claim 10 wherein the arithmetical product of said cross-sectional metal area and relative magnetic permeability of said core member is at least twice the arithmetical product of said known piping metal area and piping permeability.

12. The pipe-inspection apparatus of claim 10 wherein said relative magnetic permeability of said core member is no more than about half of said known piping permeability.

13. The pipe-inspection apparatus of claim 10 further including:
- a well-logging cable connected to said body and cooperatively arranged for moving said body through selected depth intervals in such a piping string; and
- recording means coupled to said cable and cooperatively arranged for respectively recording said defect and thickness output signals as a function of the depth interval at which each of said output signals is obtained.

14. The pipe-inspection apparatus of claim 13 further including:
- signal-processing means cooperatively arranged between said cable and said recording means for momentarily delaying said output signals from one of said circuit means obtained at a given depth interval until said output signals from the other of said circuit means are obtained at said given depth interval.

* * * * *